United States Patent
Yaginuma et al.

(10) Patent No.: US 8,367,115 B2
(45) Date of Patent: Feb. 5, 2013

(54) PROCESS FOR PRODUCTION OF CRYSTALLINE CELLULOSE AND TABLETS CONTAINING GRANULES

(75) Inventors: Yoshihito Yaginuma, Tokyo (JP); Naoya Yoshida, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 198 days.

(21) Appl. No.: 12/675,215

(22) PCT Filed: Aug. 26, 2008

(86) PCT No.: PCT/JP2008/065170
§ 371 (c)(1),
(2), (4) Date: Feb. 25, 2010

(87) PCT Pub. No.: WO2009/028487
PCT Pub. Date: Mar. 5, 2009

(65) Prior Publication Data
US 2010/0209504 A1    Aug. 19, 2010

(30) Foreign Application Priority Data
Aug. 27, 2007   (JP) .................................. 2007-219299

(51) Int. Cl.
*A61K 9/14*   (2006.01)
*A61K 9/20*   (2006.01)
*A61K 9/48*   (2006.01)

(52) U.S. Cl. ......... 424/489; 424/451; 424/464; 424/490

(58) Field of Classification Search ................ None
See application file for complete search history.

(56) References Cited

U.S. PATENT DOCUMENTS

| | | |
|---|---|---|
| 4,159,345 A | 6/1979 | Takeo et al. |
| 5,384,130 A | 1/1995 | Kamada |
| 5,505,983 A | 4/1996 | Kamada |
| 2004/0053887 A1 * | 3/2004 | Obae et al. .................. 514/57 |
| 2006/0147516 A1 | 7/2006 | Habib et al. |
| 2006/0147517 A1 | 7/2006 | Habib et al. |
| 2007/0028801 A1 | 2/2007 | Yamasaki et al. |
| 2009/0022791 A1 * | 1/2009 | Obae et al. ................. 424/464 |

FOREIGN PATENT DOCUMENTS

| | | |
|---|---|---|
| JP | 53-127553 | 11/1978 |
| JP | 3-258730 | 11/1991 |
| JP | 4-20889 | 4/1992 |
| JP | 7-173050 | 7/1995 |
| WO | 2002/002613 | 1/2002 |
| WO | 2004/106416 | 12/2004 |
| WO | 2005/041934 | 5/2005 |
| WO | 2005/084636 | 9/2005 |
| WO | 2006/074185 | 7/2006 |
| WO | WO 2006074185 A2 * | 7/2006 |
| WO | 2007/066646 | 6/2007 |

OTHER PUBLICATIONS

Beckert et al., "Compression of enteric-coated pellets to disintegrating tablets," Int. J. Pham., vol. 143, pp. 13-23, 1996.

* cited by examiner

*Primary Examiner* — Susan Tran
(74) *Attorney, Agent, or Firm* — Greenblum & Bernstein, P.L.C.

(57) ABSTRACT

A process for producing a granule-containing tablet comprising mixing more than 25 mass % to 89 mass % or less of crystalline cellulose exhibiting a tensile displacement at break of 25 to 80 μm and a relative fluidity index of 2.15 to 2.80 at a maximum compaction stress of 15 kPa, 10 to 70 mass % of spherical granules, and 20 mass % or less of a disintegrant, and then compressing the obtained mixture.

11 Claims, No Drawings

PROCESS FOR PRODUCTION OF CRYSTALLINE CELLULOSE AND TABLETS CONTAINING GRANULES

TECHNICAL FIELD

The present invention relates to a tablet containing a granular agent for a pharmaceutical preparation, particularly film-coated granules.

BACKGROUND ART

A tablet is the most widely used dosage form among pharmaceutical solid agents from the viewpoints of properties such as medication taking, transportability, and preservation. Medicines are incorporated into tablets in various shapes and sizes. Among them, spherical granules having a spherical form and narrow particle size distribution as represented by film-coated granules cannot be tableted by themselves due to their low compactibility. It is also not desirable to cause deformation in granules by pressure during tableting. For the above reasons, spherical granules are mixed with other additives upon tableting.

However, even when such spherical granules are mixed with other powder substances, separation and segregation occur during transfer from a mixer to a hopper, from a hopper to a tableting machine, and within a tableting machine; therefore, it is difficult to obtain a tablet having a uniform content.

There is a case in which crystalline cellulose which is superior in compression compactibility is used as an additive (for example, patent documents 1 and 2, and non-patent document 1). Also, a technology for coating film-coated granules with a fibrous excipient by an oily substance to prevent damage to a film of the granules during tableting is disclosed (patent document 3). Further, a technology directed to obtain a bitterness-masked, orally-disintegrating tablet as a granule-containing tablet having film-coated granules is disclosed (patent document 4). Furthermore, a technology directed to obtain a granule-containing tablet which maintains zero-order release control after the granule-containing tablet is made from film-coated granules having a controlled release of an active ingredient is disclosed (patent document 5).

Patent Document 1: JP 3-258730 A
Patent Document 2: International Publication WO2005/084636 Pamphlet
Patent Document 3: JP 4-20889 B
Patent Document 4: International Publication WO2006/074185 Pamphlet
Patent Document 5: International Publication WO2005/041934 Pamphlet
Non-Patent Document 1: T. E. Beckert, K. Lehmann, P. C. Schmidt, Compression of enteric-coated pellets to disintegrating tablets, Int. J. Pharm., 1996, vol. 143, p. 13-23

DISCLOSURE OF THE INVENTION

Problems to be Solved by the Invention

An object of the present invention is to provide crystalline cellulose which is suitable for producing a tablet containing spherical granules including film-coated granules. Further, an object of the present invention is to provide a granule-containing tablet in which separation and segregation do not occur easily.

Means for Solving the Problems

However, patent document 1, patent document 2, and non-patent document 1 mainly disclosed that damages to granules during tableting were prevented by a high compactibility of the crystalline cellulose, but did not disclose at all that crystalline cellulose having a specific physical property was effective for preventing separation and segregation. Further, while the method disclosed in patent document 3 is effective for preventing separation and segregation, there has been a problem that operation of the method is cumbersome. Furthermore, although disclosures about a granule-containing tablet are found in patent document 4 and patent document 5, they are directed to particular effects; namely, patent document 4 discloses an orally-disintegrating tablet and patent document 5 discloses a granule-containing tablet exhibiting zero-order release. It has not been disclosed in either of the above documents at all that crystalline cellulose having the specific physical property is effective for preventing separation and segregation between granules and additives.

As the result of intensive studies on excipients for tableting to solve the aforementioned problems, the present inventors have found that a tablet containing constant amount of spherical granules can be continuously produced without causing separation and segregation between granules and excipients by mixing crystalline cellulose having the specific powder property and spherical granules, and optionally disintegrants, and then compressing the obtained mixture. The present invention has been accomplished thereby. Specifically, the present invention is as follows.

(1) A process for producing a granule-containing tablet comprising mixing more than 25 mass % to 89 mass % or less of crystalline cellulose exhibiting a tensile displacement at break of 25 to 80 μm and a relative fluidity index of 2.15 to 2.80 at a maximum compaction stress of 15 kPa, 10 to 70 mass % of spherical granules, and 20 mass % or less of a disintegrant, and then compressing the obtained mixture.

(2) The method for producing the granule-containing tablet according to (1), wherein the tensile displacement at break is 30 to 65 μm.

(3) The method for producing the granule-containing tablet according to (1) or (2), wherein the relative fluidity index is 2.55 to 2.75.

(4) The method for producing the granule-containing tablet according to any one of (1) to (3), wherein the disintegrant is partially-pregelatinized starch.

(5) The method for producing the granule-containing tablet according to any one of (1) to (4), wherein the spherical granules are film-coated granules.

(6) The method for producing the granule-containing tablet according to (5), wherein the film-coated granules comprise spherical core particles containing 70 mass % or more of a crystalline cellulose component, a medicine layer coating the periphery of the spherical core particles, and a film covering the periphery of the medicine layer.

(7) The method for producing the granule-containing tablet according to (5) or (6), wherein the average particle diameter of the film-coated granules is 300 μm or less.

(8) A granule-containing tablet obtainable by the method according to (1) to (7).

(9) A granule-containing tablet comprising more than 25 mass % to 89 mass % or less of crystalline cellulose exhibiting a tensile displacement at break of 25 to 80 μm and a relative fluidity index of 2.15 to 2.80 at a maximum compaction stress of 15 kPa, 10 to 70 mass % of spherical granules, and 20 mass % or less of a disintegrant.

(10) A crystalline cellulose excipient for a granule-containing tablet, wherein the crystalline cellulose excipient comprises more than 25 mass % to 89 mass % or less of crystalline cellulose exhibiting a tensile displacement at break of 25 to 80

μm and a relative fluidity index of 2.15 to 2.80 at a maximum compaction stress of 15 kPa, and 20 mass % or less of a disintegrant.

(11) Use of a crystalline cellulose composition comprising more than 25 mass % to 89 mass % or less of crystalline cellulose exhibiting a tensile displacement at break of 25 to 80 μm and a relative fluidity index of 2.15 to 2.80 at a maximum compaction stress of 15 kPa, and 20 mass % or less of a disintegrant, as an excipient for a granule-containing tablet.

Advantages of the Invention

The present invention has such an effect that a granule-containing tablet having less separation and segregation can be produced with a high productivity.

BEST MODE FOR CARRYING OUT THE INVENTION

The present invention is described specifically hereinbelow.

Crystalline cellulose used for producing the granule-containing tablet of the present invention exhibits a tensile displacement at break of 25 to 80 μm.

A "tensile displacement at break" as used in the present invention is expressed as an amount of displacement. Namely, the crystalline cellulose of the present invention is filled in a cell having a cylindrical space with an inner diameter of 25 mm and height of 40 mm, which is designed to split into top and bottom halves in the middle, and pressed from above with a circular plate having a diameter of 25 mm and a thickness of 3 mm, and compressed downwardly at a speed of 0.1 mm/s, and held for 60 seconds with the same compression force after compression force has reached 300N. And then, a top cell is pulled upwardly at a speed of 0.4 mm/s. An amount of displacement observed from the time of pulling the top cell to the time when a powder layer is broken represents the "tensile displacement at break." A tensile displacement at break is an index of resistance of a powder layer. The powder layer as used herein refers to an assembly powder sample of crystalline cellulose.

A commercially available device which is capable of carrying out measurements as described above include Aggrobot (trade name) (AGR-1), a product of Hosokawa Micron Corporation; however, other devices can be used as long as they are capable of carrying out measurements as described above. It is to be noted that values of tensile displacement at break in the present specification are the values obtained by Aggrobot (trade name) (AGR-1), a product of Hosokawa Micron Corporation.

When a tensile displacement at break is less than 25 μm, resistance against spherical granules is reduced and separation and segregation become large. Further, when a tensile displacement at break exceeds 80 μm, fluidity of powder for tableting decreases and variation in tablet weight tends to become large. It is particularly preferable that a tensile displacement at break is 30 to 65 μm.

Further, crystalline cellulose used for producing the granule-containing tablet of the present invention exhibits a relative fluidity index of 2.15 to 2.80 at a maximum compaction stress of 15 kPa. When a shear stress is applied to a powder layer which is under a certain normal stress from a lateral direction, the powder layer starts to slide in a shearing direction as the shear stress has reached a certain level. A maximum compaction stress refers to slipperiness (fluidity) as observed above. In the present invention, a powder sample is pre-compacted with a predetermined stress, then shear tests are carried out with six points of normal stress, all of which are the same as or lower than the above predetermined stress, and a uniaxial collapse stress and a maximum compaction stress are obtained from the results thus obtained. Subsequently, a uniaxial collapse stress and a maximum compaction stress are similarly obtained with varied pre-compaction stresses.

In the present invention, measurements are conducted under the following conditions; the normal stresses in measurements with the pre-compaction stress of 3 kPa are 0.80, 1.00, 1.40, 1.70, 2.00, and 2.30 kPa, the normal stresses in measurements with the pre-compaction stress of 6 kPa are 1.50, 2.10, 2.70, 3.30, 3.90, and 4.50 kPa, and the normal stresses in measurements with the pre-compaction stress of 9 kPa are 2.30, 3.10, 4.10, 5.00, 5.90, and 6.80 kPa. Data of three pairs of uniaxial collapse stresses and maximum compaction stresses thus obtained are plotted and straight-line approximation is performed by a method of least-squares to obtain a regression equation. Then, the uniaxial collapse stress (kPa) at the maximum compaction stress of 15 kPa is calculated based on the regression equation to obtain the relative fluidity index (=15/uniaxial collapse stress).

In general, a similar measurement is carried out with one point of pre-compaction stress to obtain a maximum compaction stress and a uniaxial collapse stress, from which a value of Flow Function (FF) (=maximum compaction stress/uniaxial collapse stress) is obtained. When a powder layer having a unit area receives a uniaxial stress (normal stress), it will slide at a maximum compaction stress. This indicates that the larger the maximum compaction stress is, the worse the fluidity of the powder is. That is, it is indicated that the larger the FF is, the better the fluidity is. However, it is normal that a maximum compaction stress and a uniaxial collapse stress change depending on pre-compaction, and thus FF, which is a ratio between a maximum compaction stress and a uniaxial collapse stress, also fluctuates. Therefore, in order to raise an accuracy, a maximum compaction stress and a uniaxial collapse stress were obtained with various precompaction stresses, and an approximate equation was calculated based on data of three points, and so-called FF was calculated at the maximum compaction stress of 15 kPa as shown above in the present invention. However, because the FF thus obtained is different from a method which is calculated out in general, it is called "relative fluidity index" in the present invention to avoid any misunderstanding.

While a relative fluidity index can be measured by a Jenike shear Tester, a parallel flat plate-type shear tester, a ring cell-type shear tester, and the like, a device which automatically conducts precompaction and measurement is available recently, and use of such a device is preferable in view of an improvement in accuracy. Specifically, Shear Scan (trade name) TS-12 model, a product of Sci-Tec Inc., and the like can be used. Values of the relative fluidity index in the present specification are the values obtained by using Shear Scan (trade name) TS-12 model, a product of Sci-Tec Inc. When a relative fluidity index is less than 2.15, fluidity of powder prior to tableting is poor and variability in tablet weight becomes large, while when it exceeds 2.80, separation and segregation are likely to become large. Particularly preferably, it is in a range of 2.55 to 2.75.

Crystalline cellulose used for producing the granule-containing tablet of the present invention can be either single kind or a mixture of plural crystalline cellulose as long as it satisfies both the tensile displacement at break and the relative fluidity index as described above. However, after searching through existing crystalline cellulose, no crystalline cellulose was found to satisfy the tensile displacement at break and the relative fluidity index defined by the present invention at the same time. Furthermore, when existing crystalline cellulose was used as an excipient for the granule-containing tablet, it was not satisfactory in regards of separation and segregation. Therefore, crystalline cellulose used for producing the granule-containing tablet of the present invention is preferably obtained by mixing two or more kinds of crystalline cellulose.

Among them, crystalline cellulose used for producing the granule-containing tablet of the present invention is preferably obtained by mixing crystalline cellulose having a high-average ratio of minor axis to major axis and crystalline cellulose having a low-average ratio of minor axis to major axis. A "high-average ratio of minor axis to major axis" as used herein means that a particle is relatively spherical with a ratio of minor axis to major axis (average ratio of minor axis to major axis) of approximately 0.6 or above. Also, a "low-average ratio of minor axis to major axis" means that a particle is relatively rod-shaped with an average ratio of minor axis to major axis of approximately less than 0.6. It is to be noted that an average ratio of minor axis to major axis is a value represented by the following formula, in which $D_{50}$ refers to a 50% value cumulated in a cumulative under sieve distribution of minor axes, and $L_{50}$ refers to a 50% value cumulated in a cumulative under sieve distribution of major axes.

An average ratio of minor axis to major axis=$D_{50}/L_{50}$

Each kind of crystalline cellulose can be produced by a publicly known method. For example, crystalline cellulose having a low-average ratio of minor axis to major axis can be produced by a method disclosed in JP 53-127553A and the like. An average particle diameter is preferably smaller than but close to spherical granules of interest. For example, when a tablet containing spherical granules having an average particle diameter of approximately 400 μm is produced, an average particle diameter of the crystalline cellulose is preferably 70 μm or greater, more preferably 150 μm or greater. Also, crystalline cellulose having the low-average ratio of minor axis to major axis can be produced by methods disclosed in a pamphlet of International Publication WO02/02643A1, a pamphlet of WO2004/106416A1, and the like.

Fluidity deteriorates when the average particle diameter of the crystalline cellulose is either too small or too large. The average particle diameter is preferably approximately 20 to 100 μm, more preferably approximately 25 to 80 μm, and even more preferably approximately 30 to 70 μm.

Crystalline cellulose used for the granule-containing tablet of the present invention can be obtained by appropriately mixing the crystalline celluloses as described above so that the obtained crystalline cellulose has a range of "a tensile displacement at break of 25 to 80 μm and a relative fluidity index of 2.15 to 2.80", furthermore a range of "a tensile displacement at break of 30 to 65 μm", and "a relative fluidity index of 2.55 to 2.75."

As will be described in Examples in detail, for example, when crystalline cellulose a having the average ratio of minor axis to major axis of 0.357, the average particle diameter of 49 μm, the tensile displacement at break of 83.5 μm, and the relative fluidity index of 1.83, and crystalline cellulose b having the average ratio of minor axis to major axis of 0.726, the average particle diameter of 172 μm, the tensile displacement at break of 41.0 μm, and the relative fluidity index of 3.29 were mixed, a mass ratio of a:b=3:7 was the most optimal. And the tensile displacement at break and the relative fluidity index of the obtained crystalline cellulose were 58.9 μm and 2.68, respectively. Also, when crystalline cellulose a and crystalline cellulose c having the average ratio of minor axis to major axis of 0.647, the average particle diameter of 98 μm, the tensile displacement at break of 44.4 μm, and the relative fluidity index of 3.12 were mixed, the mass ratio of a:c=6:4 was the most optimal. And the tensile displacement at break and the relative fluidity index of the obtained crystalline cellulose were 59.8 μm and 2.19, respectively.

An amount of the crystalline cellulose of the present invention to be incorporated is more than 25 mass % to 89 mass % or less. Considering a balance between fluidity and compactibility, it is preferably 30 to 80 mass %, and particularly preferably 30 to 70 mass %. When the amount of crystalline cellulose incorporated exceeds 89 mass %, fluidity is impaired and an amount of spherical granules to be incorporated decreases, and thus a content of medicine cannot be increased. Therefore, it is not preferable. On the other hand, when the amount of crystalline cellulose incorporated is 25 mass % or less, crystalline cellulose will be caught in spaces between spherical granules, and thus an effect of inhibiting separation and segregation and an effect of compactibility exerted by crystalline cellulose cannot be obtained. Thus, it is not preferable.

It is to be noted that "crystalline cellulose" as used in the present invention refers to ones which conform to a standard for "crystalline cellulose" set forth in the Japanese Pharmacopoeia, Fifteenth Edition.

Spherical granules used for producing the granule-containing tablet of the present invention refer to granules having an average ratio of minor axis to major axis of 0.8 or more and a minor axis distribution coefficient of 0.6 or more. Here, a minor axis distribution coefficient is a value represented by the following formula, wherein $D_{10}$ refers to a 10% value cumulated, and $D_{90}$ refers to a 90% value cumulated in a cumulative under sieve distribution of minor axes.

A minor axis distribution coefficient=$D_{10}/D_{90}$

Extrusion-granulated granules, extrusion-granulated/spheronized granules (extrusion-marumerized granules), stirring-granulated granules, stirring-granulated/spheronized granules, tumbling fluidized bed-granulated granules, layering granules, granules having spherical core particles to which a water-soluble medicine is adsorbed and supported, granules obtained by applying film-coating to the above-described granules, and the like can be provided as a kind of spherical granules. The above-described granules are likely to segregate during tableting, and also are often inferior in compactibility. Particularly, in regard to film-coated granules obtained by applying extrusion-marumerized granules or layering granules to sustained-release film-coating, enteric film-coating, and the like, although application of film-coating is easy owing to those high degree of spheronization, production of the granule-containing tablet comprising them has been often difficult because the granules and excipients are more likely to segregate during tableting. In view of the above, such film-coated granules are preferable because it can fully enjoy a significance of the present invention.

Among them, film-coated granules obtained by applying film-coating to layering granules are particularly preferable in view of those sharper particle size distribution and high average ratio of minor axis to major axis.

Layering granules used herein mean granules obtained by coating the periphery of the surface of spherical core particles with a medicine layer, and the spherical core particles are preferably made of crystalline cellulose. Spherical core particles made of crystalline cellulose preferably contain 30 mass % or more of crystalline cellulose. The higher the content of crystalline cellulose is, the higher the strength becomes; therefore, the content of crystalline cellulose is more preferably 70 mass % or more, and further, particularly preferably 100 mass %. Examples of spherical core particles made of crystalline cellulose include Celphere (trade name) (a product of Asahi Kasei Chemicals Corporation). The average ratio of minor axis to major axis of spherical core particles is 0.8 or more, and the average particle diameter of the same is approximately 50 to 1000 μm.

Components other than crystalline cellulose which may be contained in spherical core particles can be exemplified by additives which are ordinarily used for preparation of a pharmaceutical product, for example, excipients such as lactose, sucrose, D-mannitol, corn starch, powder cellulose, calcium hydrogen phosphate, and calcium carbonate; disintegrants such as hydroxypropyl cellulose having a low degree of substitution, carmellose calcium, partially-pregelatinized starch, croscarmellose sodium, crospovidone, and carboxymethyl starch; binders such as hydroxypropyl cellulose, povidone, and xanthan gum; coating agents such as hydroxypropyl methylcellulose, methacrylic acid copolymer LD, and an aqueous dispersion liquid of ethyl cellulose; emulsifiers such as sucrose fatty acid ester, glycerin fatty acid ester, sodium lauryl sulfate, and polysorbate 60; other additives such as talc, magnesium stearate, magnesium aluminometasilicate, titanium oxide, light silicic acid anhydride, and crystalline cellulose carmellose sodium.

As an amount of spherical granules incorporated is increased, a content of medicine is correspondingly increased; therefore, it is preferable that way. However, in order to secure practical tablet hardness, an amount of spherical granules to be incorporated needs to be 70 mass % or less. It is preferably 65% or less, and more preferably 60 mass % or less.

Further, at least, spherical granules need to be incorporated at 10 mass % at lowest, preferably at 15 mass % or more, and even more preferably at 30 mass % or more.

At this point, a method to obtain film-coated granules using spherical core particles is described in detail.

To layer (coat) spherical core particles with a medicine-containing layer, publicly known devices such as a centrifugal fluidized coating device (such as "CF granulator" (trade name), a product of Freund Corporation) and a fluidized bed coating device are used. As for fluidized bed coating devices, besides an ordinary fluidized bed-type, a spouted-bed type having a guide tube (Wurster column) inside thereof, a tumbling fluidized bed-type having a rotation mechanism at the bottom thereof, and the like can be used. Examples of the devices include "Flow Coater" (trade name) and "Spir-a-flow" (trade name), both products of Freund Corporation, "WST/WSG series" (trade name) and "GPCG series" (trade name), both products of Glatt GmbH, "New-Marumerizer" (trade name), a product of Fuji Paudal Co., Ltd., and "Multiplex" (trade name), a product of Powrex Corporation.

To supply a layering liquid, methods suitable for each device such as top spraying, bottom spraying, side spraying, and tangential spraying can be selected, and the layering liquid is sprayed on spherical core particles. While the layering liquid is sprayed on spherical core particles continuously or intermittently, it is dried to form a medicine-containing layer. At this time, to avoid aggregation of the particles or dusting of the spraying liquid caused by drying prior to attaching to core particles, it is preferable to optimize an amount of hot air, rotation speed of the rotation mechanism, spray pressure of a medicine-containing spray liquid, and the like. Upon completion of spraying of the layering liquid, spherical elementary granules are dried. At this time, the spherical elementary granules can be, without taking samples out, dried in the same condition or by adjusting an amount of air and temperature appropriately.

As layering liquids, solution or suspension of medicine is used. Although it can be made as an organic solvent-based liquid, it is preferably made as a water-based liquid in view of conservation of operational environment and natural environment. A concentration of medicine in the layering liquid is preferably approximately 5 to 30 mass %, while it depends on solubility, viscosity, and suspensibility of the medicine. Other pharmaceutical additives can be incorporated into the layering liquid as needed.

Among those pharmaceutical additives, a most effective one is a water-soluble polymer compound (binder), which can increase strength of a medicine-containing layer. Specific examples of water-soluble polymer compound binders include hydroxypropylcellulose, hypromellose (hydroxypropyl methylcellulose), methylcellulose, carmellose sodium, pregelatinized starch, gum arabic powder, carboxyvinyl polymer, povidone (polyvinylpyrrolidone), polyvinyl alcohol, carrageenan, xanthan gum, and pullulan. It is also effective to incorporate crystalline cellulose carmellose sodium to improve suspension stability of medicine particles in a case when the layering liquid is the aqueous suspension liquid, and to prevent detachment of the medicine-containing layer in spherical elementary granules.

It is also possible to, instead of the layering liquids such as aqueous solution or aqueous suspension containing the medicine and the water-soluble polymer compound, simultaneously supply medicine powders and aqueous binder solution to spherical core particles. When using the above method, additives other than the medicine, for example, excipients, can be used by appropriately mixing them with the medicine powders.

An amount of the medicine-containing layer for coating is decided based on formulation designs such as dose per administration and size of a preparation. However, if an example has to be given, the amount is approximately 0.5 to 200 mass % with respect to spherical core particles.

A "medicine" as used in the present invention refers to one which is used for treatment, prevention, and diagnosis of a disease in humans or animals, and which is administered to a body orally. Specific examples include ones described below; anti-epileptic agents (phenyloin, acetylpheneturide, trimethadione, phenobarbital, primidone, nitrazepam, sodium valproate, sultiame, and the like), antipyretic-analgesic and anti-inflammatory agents (acetaminophen, phenylacetylglycine methyl amide, mefenamic acid, diclofenac sodium, floctafenine, aspirin, aspirin aluminum, ethenzamide, oxyphenbutazone, sulpyrine, phenylbutazone, ibuprofen, alclofenac, naloxone, ketoprofen, tinoridine hydrochloride, benzydamine hydrochloride, tiaramide hydrochloride, indomethacin, piroxicam, salicylamide, and the like), antivertigo agents (dimenhydrinate, meclizine hydrochloride, difenidol hydrochloride, and the like), narcotics (opium alkaloid hydrochloride, morphine hydrochloride, codeine phosphate, dihydrocodeine phosphate, oxymetebanol, and the like), neuropsychiatric agents (chlorpromazine hydrochloride, levomepromazine maleate, perazine maleate, propericiazine, perphenazine, chlorprothixene, haloperidol, diazepam, oxazepam, oxazolam, mexazolam, alprazolam, zotepine, and the like), skeletal muscle relaxants (chlorzoxazone, chlorphenesin carbamate, chlormezanone, pridinol mesylate, eperisone hydrochloride, and the like), autonomic nerve agents (bethanechol chloride, neostigmine bromide, pyridostigmine bromide, and the like), anti-spasmodic agents (atropine sulfate, butropium bromide, butylscopolamine bromide, propantheline bromide, papaverine hydrochloride, and the like), anti-parkinsonian agents (biperiden hydrochloride, trihexyphenidyl hydrochloride, amantadine hydrochloride, levodopa, and the like), anti histaminic agents (diphenhydramine hydrochloride, dl-chlorpheniramine maleate, promethazine, mequitazine, clemastine fumarate, and the like), cardiotonic agents (aminophylline, caffeine, dl-isoproterenol hydrochloride, etilefrine hydrochloride, norfenefrine hydrochloride, ubidecarenone, and the like), antiarrhythmic agents (procainamide hydrochloride, pindolol, metoprolol tartrate, disopyramide, and the like), diuretic agents (potassium chloride, cyclopenthiazide, hydrochlorothiazide, triamterene, acetazolamide, furosemide, and the like), hypotensive agents (hexamethonium bromide, hydralazine hydrochloride, syrosingopine, reserpine, propranolol hydrochloride, captopril, methyldopa, and the like), vasoconstrictor agents (dihydroergotamine mesylate and the like), vasodilator agents (etafenone hydrochloride, diltiazem hydrochloride, carbocromen hydrochloride, pentaerythritol tetranitrate, dipyridamole, isosorbide nitrate, nifedipine, nicametate citrate, cyclandelate, cinnarizine, and the like), anti-arteriosclerotic agents (ethyl linoleate, lecithin, clofibrate, and the like), cardiovascular agents (nicardipine hydrochloride, meclofenoxate hydrochloride, cytochrome c, pyridinolcarbamate, vinpocetine, calcium hopantenate, pentoxifylline, idebenone, and the like), respiratory stimulants (dimefline hydrochloride and the like), anti-tussive expectorant agents (dextromethorphan hydrobromide, noscapine, L-methylcysteine hydrochloride, bromhexine hydrochloride, theophylline, ephedrine hydrochloride, amlexanox, and the like), cholagogues (osalmid, phenylpropanol, hymecromone, and the like), intestinal regulators (berberine chloride, loperamide hydrochloride, and the like), agents for digestive organs (metoclopramide, fenipentol, domperidone, and the like), vitamin agents (retinol acetate, dihydrotachysterol, etretinate, thiamine hydrochloride, thiamine nitrate, fursultiamine, octotiamine, cyclotiamine, riboflavin, pyridoxine hydrochloride, pyridoxal phosphate, nicotinic acid, pantethine, cyanocobalamin, biotin, ascorbic acid, phytonadione, menatetrenone, and the like), antibiotics (benzathine benzylpenicillin, amoxicillin, ampicillin, cyclacillin, cefaclor, cephalexin, cefuroxime axetil, erythromycin, kitasamycin, josamycin, chloramphenicol, tetracycline, griseofulvin, cefuzonam sodium, and the like), chemotherapeutic agents (sulfamethoxazole, isoniazid, ethionamide, thiazosulfone, nitrofurantoin, enoxacin, ofloxacin, norfloxacin, and the like).

A case in which film-coating is applied to spherical elementary granules is then described.

Film-coating is conducted with aims to adjust a dissolution rate of medicine (sustained-release, enteric release, timed-release, pulsatile release, masking bitterness, and the like), prevent moisture, add color, and the like. For film-coating, acrylic resin-based coating agents such as dispersion liquid of ethyl acrylate/methyl methacrylate copolymer, aminoalkyl methacrylate copolymer E, aminoalkyl methacrylate copolymer RS, methacrylic acid copolymer L, methacrylic acid copolymer LD, and methacrylic acid copolymer S; cellulose-based coating agents such as ethyl cellulose, aqueous dispersion liquid of ethyl cellulose, carboxymethyl ethyl cellulose, cellulose acetate phthalate, hypromellose phthalate, and hydroxypropyl methylcellulose acetate succinate; vinyl acetate resin-based coating agents such as aqueous dispersion liquid of vinyl acetate resin; and the like can be used. Additives such as plasticizers, inorganic particles, and water-soluble substances can be incorporated to adjust film-formability, a coating property, stability, and releasability.

While the film-coating agent can be used by dissolving it in an organic solvent, it is preferably used in an aqueous-based solvent in view of conservation of operational environment and natural environment. Latex-type coating agents such as dispersion liquid of ethyl acrylate/methyl methacrylate copolymer, methacrylic acid copolymer LD, aqueous dispersion liquid of ethyl cellulose, and aqueous dispersion liquid of vinyl acetate resin are particularly preferable.

Film-coating is performed using a device similar to the ones used for layering. To supply the film-coating liquid, methods suitable for each device such as top spraying, bottom spraying, side spraying, and tangential spraying can be selected, and the film-coating liquid is sprayed on spherical elementary granules. Upon completion of spraying of the film-coating liquid, film-coated granules can be dried, without taking samples out, in the same condition or by adjusting an amount of air and temperature appropriately. After that, aggregated coarse particles are screened out as needed, and the resulting film-coated granules are used as raw materials for a granule-containing tablet.

An average particle diameter of film-coated granules is approximately 50 to 1000 μm. However, smaller size is preferable because separation and segregation become less frequent during tableting and also damages to a film by pressure during tableting are reduced. Particularly preferably, the average particle diameter is 300 μm or less.

As disintegrants used for producing the granule-containing tablet of the present invention, carmellose, carboxymethyl starch sodium, carmellose calcium, croscarmellose sodium, crospovidone, hydroxypropyl cellulose having a low degree of substitution, partially-pregelatinized starch, and the like are used. A particularly preferable disintegrant is partially-pregelatinized starch, and commercial products thereof include PCS (trade name) (a product of Asahi Kasei Chemicals Corporation) and Starch 1500 (a product of Colorcon., Inc.) An amount of disintegrants incorporated is 20 mass % or less, preferably 1 to 20 mass %, particularly preferably 2 to 15 mass %. When amount of disintegrants incorporated is more than 20 mass %, there is a case that compactibility of a tablet decreases and a tablet disintegrates to form an unmixed lump, and thus disintegrating property is adversely impaired. Thus, it is not preferable.

The granule-containing tablet of the present invention is produced by appropriately mixing crystalline cellulose, spherical granules, disintegrants as needed, as have been described above, and further, additives such as fluidizing agents and lubricants, and then compressing (tableting) the obtained mixture. As for spherical granules, for example, plural kinds of film-coated granules having different dissolution rates can be incorporated. Also, medicine powders can be incorporated with additives for purposes such as increasing an initial release amount.

For mixing of the granule-containing tablet of the present invention, publicly known devices such as a V-type mixer and a tumbler mixer can be used. Attention should be paid because if uniform mixing is not achieved at this point, non-uniformity will be carried on to a tableting step. When incorporating a lubricant, it is added after other raw materials are thoroughly mixed, and then the mixture is lightly mixed.

Subsequently, the obtained powders for tableting are filled in a hopper of a tableting machine to perform tableting. At this time, attention should be paid because powders separate and segregate during discharge and filling as well. It is preferable to perform tableting using a forced feeder. Although faster tableting speed provides superior productivity, speed should be determined based on a balance between degree of separation and segregation, and tablet hardness. Tablet hardness is affected by tableting pressure the most, and in fear of damages to a film and the like, tableting pressure should be set at the minimum necessary, namely, such a pressure that tablet hardness becomes approximately 50 to 80 N. Further, film-coating can be performed on the obtained tablet for the purposes of moisture prevention, coloring, light shielding, and the like.

EXAMPLES

The present invention is explained based on Examples. Methods for measuring physical properties are collectively described hereinbelow.

<Tensile Displacement at Break (μm) of Crystalline Cellulose>

Tensile displacement at break was measured using a powder layer compression/tensile property-automatic evaluation device (a product of Hosokawa Micron Corporation, Aggrobot (trade name), AGR-1 model).

Powder samples were filled in a cell having a cylindrical space with inner diameter of 25 mm and height of 40 mm, which was designed to split into top and bottom halves (each part is 20 mm high), and then weighed. After tapping it 50 times, a circular plate having a diameter of 25 mm and a thickness of 3 mm was inserted from above. The cell was then set in the device and the samples were pressed downwardly at a speed of 0.1 mm/s. After compression force had reached 300N, the samples were held for 60 seconds with the same compression force. Then, a top cell was pulled upwardly at a speed of 0.4 mm/s, and displacement observed from the time of pulling the top cell to the time when the powder layer was broken was measured automatically. The above measurement was repeated three times and an average value was obtained, which was provided as tensile displacement at break. The above measurements were performed in the environment of 25° C. and 60% of relative humidity.

<Relative Fluidity Index of Crystalline Cellulose (No Unit)>

Relative fluidity index of crystalline cellulose was measured using a powder particle fluidity measurement device (a product of Sci-Tec Inc., Shear Scan (trade name), TS-12 model). Powder samples were filled in a standard type rotary separation cell container (inner diameter of 60 mm and volume of 30 mL). It was weighed and then set in the device. Then, a head cell was pulled down, and in between two parallel rings separated by a tiny space, the samples were pre-compacted at 3 kPa. Subsequently, under the condition in which the cell was loaded by each of the normal stresses ($=\sigma$) of 0.80, 1.00, 1.40, 1.70, 2.00, and 2.30 kPa, a bottom ring was moved with respect to a top ring, and shear force ($=\tau$) necessary to shear the powder layer is obtained.

At this time, the normal stress σ and the shear force τ are plotted as x axis and y axis, respectively. This plotting is called yield locus, and a y-intercept and a slope of the yield locus represent cohesive force C and an internal angle of friction θ, respectively. Based on C and θ obtained as above as well as (formula 1) and (formula 2) described below, a maximum compaction stress and a uniaxial collapse stress at a pre-compaction stress of 3 kPa were obtained.

Maximum compaction stress (kPa)=
$(A-(A^2 \sin^2 \theta - \tau^2 \cos^2 \theta)^{0.5})/\cos^2 \theta \times$
$(1+\sin \theta)-(C/\tan \theta)$ (Formula 1)

wherein, $A=\sigma+C/\tan \theta$

Uniaxial collapse stress (kPa)=$2 \times C(1+\sin \theta)/\cos \theta$ (Formula 2)

Then, uniaxial collapse stresses and maximum compaction stresses were similarly obtained with pre-compaction stress of 6 kPa and normal stresses of 1.50, 2.10, 2.70, 3.30, 3.90, and 4.50 kPa. Further, uniaxial collapse stresses and maximum compaction stresses were similarly obtained with pre-compaction stress of 9 kPa and normal stresses of 2.30, 3.10, 4.10, 5.00, 5.90, and 6.80 kPa. The above measurements were performed in the environment of 25° C. and 60% of relative humidity.

Data of three pairs of the uniaxial collapse stresses and the maximum compaction stresses thus obtained were plotted and straight-line approximation was performed by a method of least-squares to obtain a regression equation. Then, the uniaxial collapse stress (kPa) at the maximum compaction stress of 15 kPa was calculated based on the regression equation to obtain the relative fluidity index (=15/uniaxial collapse stress).

<Average Particle Diameter (μm) of Film-Coated Granules, Spherical Elementary Granules, Spherical Core Particles, and Crystalline Cellulose>

Particle size distribution was measured by sieving 10 g of samples for 15 minutes by a Ro-Tap sieve shaker (a product of Hirako Seisakusho, sieve shaker A model) using a JIS standard sieve. Then, particle diameters of 50% cumulated in a cumulative under sieve distribution were provided as an average particle diameter.

If particle size distribution for smaller particles is desired, it can be obtained by sieving 5% of sample for five minutes by an Air Jet Sieve (trade name) (a product of Hosokawa Alpine) using a JIS standard sieve, although it was not used in either Examples or Comparative Examples this time.

<Average Ratio of Minor Axis to Major Axis of Crystalline Cellulose, Spherical Core Particles, and Spherical Elementary Granules>

A shape of samples was photographed by a digital microscope (VH-7000, a product of Keyence Corporation) (using a 50× or a 100× lens), and minor axes (D) and major axes (L) of 100 particles were measured using an image analyzer (Image-Hyper (trade name), a product of InterQuest Co.) In the above measurements, the minor axes and the major axes were defined as the short side and the long side, respectively, of a bounding rectangular box circumscribing a boundary pixel, where an area of the bounding rectangular box was minimum. Then, particle diameters of 50% cumulated in cumulative under sieve distributions of the minor axes and of the major axes were represented as "$D_{50}$" and "$L_{50}$", respectively, and a ratio between them ($D_{50}/L_{50}$) was provided as an average ratio of minor axis to major axis.

<Minor Axis Distribution Coefficient of Elementary Granules (No Unit)>

In the same manner as in measurements of the average ratio of minor axis to major axis, D and L of approximately 100 samples were measured. Particle diameters of 10% and 90% cumulated in a cumulative under sieve distribution of the minor axes were represented as "$D_{10}$" and "$D_{90}$", respectively, and a ratio between them ($D_{10}/D_{90}$) was determined as a minor axis distribution coefficient.

<Dissolution Rate of Medicine>

The dissolution rate of medicine was measured according to "6.10 Dissolution Test" under General Tests, Processes and Apparatus set forth in the Japanese Pharmacopoeia. As an apparatus, "Apparatus 2" (Paddle Method) was used with a paddle rotation speed of 100 rpm, and for a dissolution medium, "1st fluid for dissolution test" was used.

<Tablet Hardness (N)>

A load was applied to a tablet diametrically by a schleuniger tablet hardness tester (a product of Freund Corporation, 6D model), and tablet hardness was represented by the load at which the tablet collapsed. This measurement was repeated 10 times, and an average value thereof was obtained.

<Degree of Abrasion of Tablet (%)>

A sample (10 g) was put in an abrasion tester (Pharma Test, a product of Japan Machinery Company), and rotated at 25 rpm for four minutes. Then, mass of the sample left on a sieve having an opening of 75 μm was measured. A degree of abrasion was calculated by the following formula. This measurement was repeated twice, and an average value thereof was obtained.

A degree of abrasion (%)=100×(10−mass (g) of the samples left on the sieve)/10

<Disintegration Time (s) of Tablet>

Disintegration time of tablet was measured according to "6.09 Disintegration Test" "1) Immediate-release preparation" under General Tests, Processes and Apparatus set forth in the Japanese Pharmacopoeia. Using NT-2HS, a product of Toyama Sangyo Co., Ltd., as a disintegration tester, a numerical average value was obtained from six samples.

<Weight Variability (%) of Tablet>

Weights of 10 samples were measured. Standard deviation of the obtained value was divided by an average weight, and the resulting value was multiplied by 100. The obtained value was provided as weight variability.

<Variability in Content of Medicine in Tablet (%) and Measured Value (No Unit)>

Spherical granules were ground as needed and immersed in pure water, and then a medicine was completely dissolved. After removing undissolved components by filtration, a content was measured by an absorbance method. An ideal content of medicine in a tablet is calculated based on the obtained value, which is provided as a target content (T).

Subsequently, contents of medicine (Y) in 10 samples were measured in the same manner. Percentage of the obtained value in the target value (H=100Y/T) was calculated, and the standard deviation (s) was divided by H, and the resulting value was multiplied by 100. The value thus obtained was provided as variability in the content of medicine. Also, an acceptance value (AV) was calculated using the following formulas according to Table 6.02-2 in "6.02 Uniformity of Dosage Units" under General Tests, Processes and Apparatus set forth in the Japanese Pharmacopoeia.

In the case of 98.5%≦H≦101.5%: AV=2.4 s
In the case of H<98.5% AV=2.4 s+98.5−H
In the case of H>101.5% AV=2.4 s+H−101.5

It is to be noted that the acceptance value of more than "15" means that the content is so far from an ideal value that it is virtually unpractical, that it lacks uniformity, or both. The acceptance value of "10" or less means a superior uniformity, and the acceptance value of "5" or less means a particularly superior uniformity.

Examples are shown hereinbelow; however, the present invention is not limited to the below-described Examples.

Example 1

Preparation of Crystalline Cellulose

A crystalline cellulose sample was prepared according to Example 2 in a pamphlet of International Publication WO02/02643A1. Commercially available SP pulp (polymerization degree of 790) (2 kg) was chopped and put into 30 L of 4 mol/L aqueous solution of hydrochloric acid, and then hydrolyzed at 40° C. for 48 hours with stirring at 10 rpm in a low-speed stirrer (a product of Ikebukuro Horo Kogyo Co., Ltd., 30LGL reactor, a blade diameter of approximately 30 cm). The resulting acid-insoluble residue was filtered using a nutsche filter, and the resulting filtration residue was further dispersed in 70 L of pure water, and then filtered. After the above washing operation was repeated four times, the mixture was transferred to a 90 L plastic bucket. Pure water was added and the mixture was stirred with a propeller (a product of HEIDON, 1200G-type, 8M/M, a blade diameter of approximately 5 cm, 100 rpm). Subsequently, pure water and aqueous solution of ammonia for neutralization were added to the mixture to obtain aqueous dispersion liquid of cellulose having a solid-content concentration of 10 mass %, pH of 6.1, and an electrical conductivity of 37 μS/cm. The obtained solution was spray-dried (supply speed of the aqueous dispersion liquid of 6 L/hr, inlet hot air temperature of 180 to 220° C., and outlet exhaust-air temperature of 50 to 70° C.) to obtain crystalline cellulose a. Measurement values were obtained as follows for crystalline cellulose a; an average polymerization degree (269), an average ratio of major axis to minor axis of particles with size of 75 μm or less (2.6), an average particle diameter (49 μm), an apparent specific volume (4.7 cm$^3$/g), an apparent tapping specific volume (2.8 cm$^3$/g), and an angle of repose (48°). Based on the above measurement values, it was confirmed that the obtained cellulose a was equivalent to the one prepared in Example 2 of the pamphlet of International Publication WO02/02643A1 (values in parenthesis were actual values, and measurements were performed according to methods described in the above-mentioned pamphlet). Other physical properties of the crystalline cellulose a are shown in Table 2 (the physical properties were measured in accordance with definitions set forth in the present specification).

Commercially available SP pulp (polymerization degree of 1030) (2 kg) was then chopped and put into 30 L of 0.14 mol/L aqueous solution of hydrochloric acid, and then hydrolyzed at 121° C. for one hour with stirring at 30 rpm. The resulting acid-insoluble residue was filtered using a nutsche filter, and the resulting filtration residue was further dispersed in 70 L of pure water, and then filtered. After the above washing operation was repeated four times, the mixture was transferred to a 90 L plastic bucket. Pure water was added and the mixture was stirred with the propeller at 500 rpm. Subsequently, pure water and aqueous solution of ammonia for neutralization were added to the mixture to obtain aqueous dispersion liquid of cellulose having a solid-content concentration of 20 mass %, pH of 6.4, and an electrical conductivity of 65 μS/cm. The obtained solution was spray-dried (supply speed of the aqueous dispersion liquid of 6 L/hr, inlet hot air temperature of 180 to 220° C., and outlet exhaust-air temperature of 50 to 70° C.) to obtain crystalline cellulose b. Physical properties of crystalline cellulose b are shown in Table 2.

Finally, crystalline cellulose a and crystalline cellulose b were mixed at a mass ratio of 3:7 (=a:b) to obtain crystalline cellulose A of the present invention. Physical properties of crystalline cellulose A are shown in Table 1.

<Preparation of Film-Coated Granules>

Spherical core particles made of crystalline cellulose (an average particle diameter of 237 μm and an average ratio of minor axis to major axis of 0.909) were put into a tumbling fluidized bed-type coating device, and an aqueous medicine dispersion liquid (3.85% riboflavin and 1.15% povidone) was sprayed for coating (layering) the particles, thereby spherical elementary granules were obtained. The obtained spherical elementary granules contained 1.95 mass % of riboflavin, and had the average particle diameter of 238 μm, and the average ratio of minor axis to major axis of 0.926. Conditions for layering were as follows:

(1) device used: Multiplex (trade name), MP-25 model (a product of Powrex Corporation)

(2) air flow: 8 m$^3$/min (3) charge-air temperature: 70 to 75° C.

(4) exhaust-air temperature: 37 to 39° C.

(5) rotor rotation speed: 250 to 300 rpm (6) amount of spherical core particles: 18 kg (7) amount of aqueous medicine dispersion liquid: 9.345 kg (8) spray speed of aqueous medicine dispersion liquid: 100 to 110 g/min (9) spray air pressure: 0.55 Mpa

(10) spray air flow: 702 NL/min

Then, while pure water (100 parts by mass) was stirred with the propeller, an aqueous ethyl cellulose dispersion liquid (a product of FMC Corporation, Aquacoat ECD) (25 mass %, 7.5 parts by mass as a solid content) was added. The mixture was stirred approximately for 10 minutes, and while stirring was continued, hypromellose (a product of Shin-Etsu Chemical Co., Ltd., TC-5E) (20 parts by mass) and titanium oxide (a product of Toho Titanium Co., Ltd, NA61) (2.5 parts by mass) were added and the mixture was stirred approximately for 15 minutes. Then, a dispersion liquid of ethyl acrylate/methyl methacrylate copolymer (a product of Deggusa GmbH, Eudragit NE30D) (25 mass %, 7.5 parts by mass as a solid content) was added and the mixture was gently stirred for approximately 10 minutes. After the mixture was ran through a sieve having an opening of 250 μm, a film-coating liquid (a solid content of 17 mass %) was prepared.

The spherical elementary granules were then put into a tumbling fluidized bed-type coating device, and sprayed and coated (film-coated) with the film-coating liquid. Subsequent to removal of particles with size of 355 μm or more by a sieve, film-coated granules were obtained. An amount of film-coat in the film-coated granules was 20 mass % (with respect to spherical core particles), and an average particle diameter was 271 μm and an average ratio of minor axis to major axis was 0.926. Dissolution rates of riboflavin were as follows: 41.0% at two hours, 64.4% at four hours, 78.5% at six hours, 87.0% at eight hours, and 92.0% at 10 hours. Conditions for the film-coating were as follows:

(1) device used: Multiplex (trade name), MP-25 model (2) air flow: 7.5 to 8 m$^3$/min (3) charge-air temperature: 45 to 50° C.

(4) exhaust-air temperature: 27 to 31° C.

(5) rotor rotation speed: 240 to 300 rpm (6) amount of spherical core particle: 10 kg (7) amount of film-coating liquid: 11.7 kg (8) spray speed of film-coating liquid: 100 to 120 g/min (9) spray air pressure: 0.6 Mpa

(10) spray air flow: 702 NL/min

<Preparation and Evaluation of Tablet Containing Film-Coated Granules>

50 mass % of the film-coated granules, 40 mass % of crystalline cellulose A, and 10 mass % of partially-pregelatinized starch (PCS (trade name), PC-10, a product of Asahi Kasei Chemicals Corporation) were mixed at 30 rpm for 20 minutes by a tumbler mixer, and followed by tableting with a rotary tableting machine (Libra 2 (trade name) with a forced feeder, a product of Kikusui Seisakusho, Ltd.). As die/punch for tableting, 36 sets of die/punch having a diameter of 8 mm and a punch concave curve radius of 12 mm were used. Tableting was performed for 50 minutes at a turntable rotation speed of 40 rpm and at a compression pressure of 5.3 kN to give a 250 mg tablet. The tablet was sampled for evaluation at an initial period of tableting (1 to 2 minutes), at an intermediate period (25 to 26 minutes), and at a late period (48 to 49 minutes).

<Results of Evaluation of the Tablet>

Results are shown in Table 3. Also, dissolution rates of the medicine (riboflavin) were as follows: 43.1% at two hours; 66.5% at four hours; 81.0% at six hours, 88.4% at eight hours; and 93.1% at 10 hours.

Both tablet hardness (69.8 to 75.9 N) and a degree of abrasion (0.04% or less) are found to be at a practical level at any tableting time, and even more, the obtained disintegration time (93 to 108 minutes) can also be said to represent sufficiently fast disintegrating property. The variability in content of medicine in question is 2% or less, and it is sufficiently low. An evaluation value is a value calculated in consideration of variability in content of medicine and a content of medicine (a difference from a target value), and the evaluation value being "5" or less means that the variability in content of medicine is extremely low. Further, almost no change was observed in the dissolution rate of medicine of the obtained tablet compared with that of the film-coated granules prior to tableting. Therefore it can be said that the obtained tablet is extremely superior as a granule-containing tablet.

Example 2

Preparation of Crystalline Cellulose

Crystalline cellulose a and crystalline cellulose b were mixed at a mass ratio of 2:8 (=a:b) to obtain crystalline cellulose B of the present invention. Physical properties of crystalline cellulose B are shown in Table 1.

<Preparation of Tablet Containing Film-Coated Granules>

A tablet containing film-coated granules was obtained in the same manner as described in Example 1 except that, as crystalline cellulose, crystalline cellulose B was used instead of crystalline cellulose A.

<Results of Evaluation of the Tablet>

Results are shown in Table 3. Also, dissolution rates of the medicine (riboflavin) were as follows: 42.8% at two hours; 66.3% at four hours; 80.5% at six hours, 88.1% at eight hours; and 92.9% at 10 hours.

Although the evaluation value exceeded "5", it was still "10" or less, therefore the tablet had a uniformity. Also, it maintains tablet physical properties such as tablet hardness and the like as well as a sustained-releasability. Therefore, it can be said that the obtained tablet is a sustained-release granule-containing tablet having a sufficient ability.

Example 3

Preparation of Crystalline Cellulose

A crystalline cellulose sample was prepared according to Example 11 in JP 53-127553 A. Commercially available KP pulp (2 kg) was chopped and put into 30 L of 2 mass % aqueous solution of sulfuric acid, and then hydrolyzed at 125° C. for 25 minutes with stirring at 30 rpm. The resulting acid-insoluble residue was filtered using a nutsche filter, and the resulting filtration residue was further dispersed in 70 L of pure water, and then filtered. After the above washing operation was repeated four times, the mixture was transferred to a 90 L plastic bucket. Pure water was added and the mixture was stirred to disperse. Subsequently, pure water and aqueous solution of ammonia for neutralization were added to the mixture to obtain aqueous dispersion liquid of cellulose having a solid-content concentration of 18.5 mass %, pH of 6.3, and an electrical conductivity of 71 µS/cm. The obtained solution was spray-dried (supply speed of the aqueous dispersion liquid of 6 L/hr, inlet hot air temperature of 180 to 220° C., and outlet exhaust-air temperature of 50 to 70° C.) to obtain crystalline cellulose c. Measurement values were obtained as follows for crystalline cellulose c; an average polymerization degree (140), an apparent specific volume (2.35 cm$^3$/g), an apparent tapping specific volume (1.67 cm$^3$/g), an angle of repose (38°), and a 200-mesh fraction (59.1 mass %). Based on the above measurement values, it was confirmed that the obtained cellulose c was equivalent to the crystalline cellulose described in JP 53-127553 A (values in parenthesis were actual values, and measurements were performed according to methods described in a pamphlet thereof). Other physical properties of crystalline cellulose c are shown in Table 2 (the physical properties were measured in accordance with definitions set forth in the present specification).

Crystalline cellulose a and crystalline cellulose c were then mixed at a mass ratio of 6:4 (=a:c) to obtain crystalline cellulose C of the present invention. Physical properties of crystalline cellulose C are shown in Table 1.

<Preparation of Tablet Containing Film-Coated Granules>

A tablet containing film-coated granules was obtained in the same manner as described in Example 1 except that, as crystalline cellulose, crystalline cellulose C was used instead of crystalline cellulose A.

<Results of Evaluation of the Tablet>

Results are shown in Table 3. Also, dissolution rates of the medicine (riboflavin) were as follows: 44.5% at two hours; 68.2% at four hours; 83.1% at six hours, 90.4% at eight hours; and 95.3% at 10 hours.

As tablet hardness of the obtained tablet is extremely high and a degree of abrasion is pronouncedly low, it is possible to reduce the tableting pressure. Since the obtained tablet receives an evaluation value of around "5" and maintains a sustained-releasability, the obtained tablet can be said to be a sustained-release granule-containing tablet having a sufficient ability.

Example 4

A tablet containing film-coated granules was obtained in the same manner as described in Example 1 except that tableting was conducted without incorporating partially-pregelatinized starch, namely, by mixing 50 mass % of the film-coated granules and 50 mass % of crystalline cellulose A. Results of evaluation of the obtained tablet are shown in Table 3.

Example 5

A tablet containing film-coated granules was obtained in the same manner as described in Example 1 except that tableting was conducted by mixing 50 mass % of the film-coated granules, 30 mass % of crystalline cellulose A, and 20 mass % of partially-pregelatinized starch as components of a granule-containing tablet. Results of evaluation of the obtained tablet are shown in Table 3.

Comparative Example 1

A tablet containing film-coated granules was obtained in the same manner as described in Example 1 except that, as crystalline cellulose, crystalline cellulose a (equivalent to Example 2 in a pamphlet of International Publication WO02/02643A1) was used instead of crystalline cellulose A of the present invention. Results of evaluation of the obtained tablet are shown in Table 3.

Comparative Example 2

A tablet containing film-coated granules was obtained in the same manner as described in Example 1 except that, as crystalline cellulose, crystalline cellulose b was used instead of crystalline cellulose A of the present invention. Results of evaluation of the obtained tablet are shown in Table 3.

Comparative Example 3

A tablet containing film-coated granules was obtained in the same manner as described in Example 1 except that, as crystalline cellulose, crystalline cellulose c (equivalent to crystalline cellulose of JP 53-127553 A) was used instead of crystalline cellulose A of the present invention. Results of evaluation of the obtained tablet are shown in Table 3.

Comparative Example 4

A tablet containing film-coated granules was obtained in the same manner as described in Example 1 except that tableting was conducted by mixing 50 mass % of the film-coated granules, 20 mass % of crystalline cellulose A, and 30 mass % of partially-pregelatinized starch as components of a granule-containing tablet. Results of evaluation of the obtained tablet are shown in Table 3.

Examples 1 to 5 are results obtained from an attempt to prepare a granule-containing tablet using crystalline celluloses A, B, and C of the present invention. As already described above, they are actual examples that superior granule-containing tablets having a good tablet physical property and reduced variability in content of granules (medicine), while maintaining sustained-releasability of the film-coated granules, were obtained. Example 1, Example 4, and Example 5 were compared in regard to the amount of partially-pregelatinized starch incorporated, namely a disintegrant, and it is understood that disintegration time of the tablet is speeded up correspondingly to an increase in the amount of partially-pregelatinized starch incorporated. It is considered that, in the case of a granule-containing tablet, variability in therapeutic effects is reduced as the tablet immediately disintegrates upon administration and scatters into individual granules. In regard to this point incorporation of partially-pregelatinized starch is preferable. However, a tendency is observed such that tablet hardness decreases correspondingly to an increase in the amount of partially-pregelatinized starch incorporated. Accordingly, it is desirable to determine the amount of partially-pregelatinized starch to be incorporated in consideration of a balance between tablet hardness and disintegrating property.

On the other hand, Comparative Examples 1 to 3 are results obtained from an attempt to prepare a granule-containing tablet using publicly known crystalline celluloses a, b, and c. Either or both of the tensile displacement at break and the relative fluidity index was/were out of the range as defined by the present invention in any of Comparative Examples 1 to 3. Therefore, an evaluation value, which was an index of uniformity in content of medicine (spherical granules), could not be maintained at "10" or less at all times while tableting was performed.

Comparative Example 4 is an example in which, while using crystalline cellulose A of the present invention, the amount of crystalline cellulose incorporated is less than the amount defined by the present invention, and the amount of partially-pregelatinized starch incorporated is greater than the amount defined by the present invention. Due to a decrease in crystalline cellulose and an increase in the amount of partially-pregelatinized starch incorporated, tablet hardness is greatly reduced. Also, owing to a reduced amount of crystalline cellulose incorporated, an effect of inhibiting separation and segregation from granules decreased. Furthermore, as the amount of partially-pregelatinized starch incorporated was excessive, disintegrating property of the tablet was adversely impaired.

Example 6

Preparation of Spherical Granules

Spherical core particles made of crystalline cellulose (an average particle diameter of 237 μm and an average ratio of minor axis to major axis of 0.909) (1.5 kg) were put in a Henschel-type high-speed mixer granulator (rotation speed of a stirring blade: 300 rpm) and stirred, and then 20 mass % aqueous solution of sodium salicylate was added at a speed of 100 g/min. Upon completion of addition, the mixture was stirred for two more minutes, and then stirring was stopped. The mixture obtained as above was provided as a batch, and the above procedure was repeated until an amount necessary to carry out the subsequent experiments was obtained. The obtained wet granules were dried in a hot air dryer at 60° C. for about 16 hours, and coarse particles were removed by a sieve, thereby spherical granules containing sodium salicylate were obtained. The average particle diameter and the average ratio of minor axis to major axis of the obtained granules were 238 μm and 0.912, respectively.

<Preparation and Evaluation of Granule-Containing Tablet>

50 mass % of the spherical granules containing sodium salicylate and 49.5 mass % of crystalline cellulose A were mixed at 30 rpm for 20 minutes by a tumbler mixer, and then 0.5 mass % of magnesium stearate was added. The mixture was mixed for five more minutes, followed by tableting with a rotary tableting machine (Libra 2 (trade name) with a forced feeder). As die/punch for tableting, 12 sets of die/punch having a diameter of 8 mm and punch concave curve radius of 12 mm were set in a turntable at an interval of two empty spaces between each set of them. Tableting was performed for 15 minutes at a turntable rotation speed of 40 rpm and at a compression pressure of 10 to 22 kN to give a 250 mg tablet. The tablet was sampled for evaluation at an initial period of tableting (1 to 2 minutes), at an intermediate period (9 to 10 minutes), and at a late period (14 to 15 minutes). Results thus obtained are shown in Table 4.

Example 7

A tablet was obtained in the same manner as described in Example 6 except that 70 mass % of the spherical granules containing sodium salicylate, 29.5 mass % of crystalline cellulose A, and 0.5 mass % of magnesium stearate were used as components of a granule-containing tablet. Results of evaluation of the obtained tablet are shown in Table 4.

Example 8

A tablet was obtained in the same manner as described in Example 6 except that 15 mass % of the spherical granules containing sodium salicylate, 84.5 mass % of crystalline cellulose A, and 0.5 mass % of magnesium stearate were used as components of a granule-containing tablet. Results of evaluation of the obtained tablet are shown in Table 4.

In Examples 6 to 8, crystalline cellulose A was used, and the amounts of crystalline cellulose A, the spherical granules, and partially-pregelatinized starch incorporated were compared. In any of the above Examples, as a result of an attempt to prepare a granule-containing tablet, the content uniformity was found to be favorable.

Example 9

A granule-containing tablet was obtained in the same manner as described in Example 6 except that, as crystalline cellulose, crystalline cellulose B was used instead of crystalline cellulose A. Results of evaluation of the obtained table are shown in Table 4.

Example 10

A granule-containing tablet was obtained in the same manner as described in Example 6 except that, as crystalline cellulose, crystalline cellulose C was used instead of crystalline cellulose A. Results of evaluation of the obtained tablet are shown in Table 4.

Example 11

Preparation of Crystalline Cellulose

A crystalline cellulose sample was prepared according to Example 1 of a pamphlet of International Publication WO2004/106416A1. Commercially available pulp (polymerization degree of 1030) (2 kg) was chopped and put into 30 L of 4 mol/L aqueous solution of hydrochloric acid, and then hydrolyzed at 40° C. for 24 hours with stirring at 5 rpm in a low-speed mixer (a product of Ikebukuro Horo Kogyo Co., Ltd., 30LGL reactor, a blade diameter of approximately 30 cm). The resulting acid-insoluble residue was filtered using a nutsche filter, and the resulting filtration residue was further dispersed in 70 L of pure water, and then filtered. After the above washing operation was repeated four times, the mixture was transferred to a 90 L plastic bucket. Pure water was added and the mixture was stirred with a propeller (a product of HEIDON, 1200G-type, 8M/M, a blade diameter of approximately 5 cm, 5 rpm). Subsequently, pure water and aqueous solution of ammonia for neutralization were added to the mixture to obtain aqueous dispersion liquid of cellulose having a solid-content concentration of 10 mass %. The obtained solution was spray-dried (supply speed of the aqueous dispersion liquid of 6 L/hr, inlet hot air temperature of 180 to 220° C., and outlet exhaust-air temperature of 50 to 70° C.) to obtain crystalline cellulose f. Measurement values were obtained as follows for crystalline cellulose f; an average polymerization degree (310), an average particle diameter (51 μm), an apparent specific volume (8.9 cm$^3$/g), and PEG400-retention rate (275 mass %). Based on the above measurement values, it was confirmed that the obtained cellulose f was equivalent to the one prepared in Example 1 of the pamphlet of International Publication WO2004/106416A1 (values in parenthesis were actual values, and measurements were performed according to methods described in the above-mentioned pamphlet). Other physical properties of crystalline cellulose f are shown in Table 2 (the physical properties were measured in accordance with definitions set forth in the present specification).

Crystalline cellulose b and f were then mixed at a mass ratio of 4:6 (=b:f) to obtain crystalline cellulose D of the present invention. Physical properties of crystalline cellulose D are shown in Table 1.

<Preparation and Evaluation of Granule-Containing Tablet>

Then, a granule-containing tablet was obtained in the same manner as described in Example 6 except that, as crystalline cellulose, crystalline cellulose D was used instead of crystalline cellulose A. Results of evaluation of the obtained tablet are shown in Table 4.

Example 12

Preparation of Crystalline Cellulose

A crystalline cellulose sample was prepared according to Comparative Example 2 of a pamphlet of International Publication WO02/02643A1. Commercially available SP pulp (polymerization degree of 1030) (2 kg) was chopped and put into 30 L of 0.14 mol/L aqueous solution of hydrochloric acid, and then hydrolyzed at 121° C. for one hour with stirring at 30 rpm. The resulting acid-insoluble residue was filtered using a nutsche filter, and the resulting filtration residue was further dispersed in 70 L of pure water, and then filtered. After the above washing operation was repeated four times, the mixture was transferred to a 90 L plastic bucket. Pure water was added and the mixture was stirred with the propeller (500 rpm). Subsequently, pure water and aqueous solution of ammonia for neutralization were added to the mixture to obtain aqueous dispersion liquid of cellulose having a solid-content concentration of 17 mass %, pH of 6.4, and an electrical conductivity of 65 µS/cm. The obtained solution was spray-dried (supply speed of the aqueous dispersion liquid of 6 L/hr, inlet hot air temperature of 180 to 220° C., and outlet exhaust-air temperature of 70° C.) to obtain crystalline cellulose i. Measurement values were obtained as follows for crystalline cellulose i; an average polymerization degree (218), an average ratio of major axis to minor axis of particles with size of 75 µm or less (1.8), an average particle diameter (50 µm), an apparent specific volume (3.2 cm³/g), an apparent tapping specific volume (2.3 cm³/g), and an angle of repose (44°). Based on the above measurement values, it was confirmed that the obtained cellulose i was equivalent to the one prepared in Comparative Example 2 of the pamphlet of International Publication WO02/02643A1 (values in parenthesis were actual values, and measurements were performed according to methods described in the above-mentioned pamphlet). Other physical properties of crystalline cellulose i are shown in Table 2 (the physical properties were measured in accordance with definitions set forth in the present specification).

Crystalline cellulose b and i were then mixed at a mass ratio of 40:60 (=b:i) to obtain crystalline cellulose E of the present invention. Physical properties of crystalline cellulose E are shown in Table 1.

<Preparation And Evaluation of Granule-Containing Tablet>

Then, a granule-containing tablet was obtained in the same manner as described in Example 6 except that, as crystalline cellulose, crystalline cellulose E was used instead of crystalline cellulose A. Results of evaluation of the obtained tablet are shown in Table 4.

Examples 9 to 12 are results obtained from an attempt to prepare a granule-containing tablet using crystalline celluloses B, C, D, and E, instead of crystalline cellulose A. Any of the crystalline celluloses of Examples 9 to 12 exhibited a tensile displacement at break and a relative fluidity index within a range defined by the present invention, and had the favorable content uniformity as well.

Comparative Example 5

Crystalline cellulose a and b were mixed at a mass ratio of 4:6 (=a:b) to obtain crystalline cellulose d. Physical properties of crystalline cellulose d are shown in Table 1.

Then, a granule-containing tablet was obtained in the same manner as described in Example 6 except that, as crystalline cellulose, crystalline cellulose d was used instead of crystalline cellulose A of the present invention. Results of evaluation of the obtained tablet are shown in Table 4.

Comparative Example 6

Crystalline cellulose a and b were mixed at a mass ratio of 1:9 (=a:b) to obtain crystalline cellulose e. Physical properties of crystalline cellulose e are shown in Table 1.

Then, a granule-containing tablet was obtained in the same manner as described in Example 6 except that, as crystalline cellulose, crystalline cellulose e was used instead of crystalline cellulose A of the present invention. Results of evaluation of the obtained tablet are shown in Table 4.

Comparative Example 7

Crystalline cellulose b and f were mixed at a mass ratio of 3:7 (=b:f) to obtain crystalline cellulose g. Physical properties of crystalline cellulose g are shown in Table 1.

Then, a granule-containing tablet was obtained in the same manner as described in Example 6 except that, as crystalline cellulose, crystalline cellulose g was used instead of crystalline cellulose A of the present invention. Results of evaluation of the obtained tablet are shown in Table 4.

Comparative Example 8

Crystalline cellulose b and f were mixed at a mass ratio of 5:5 (=b:f) to obtain crystalline cellulose h. Physical properties of crystalline cellulose h are shown in Table 1.

Then, a granule-containing tablet was obtained in the same manner as described in Example 6 except that, as crystalline cellulose, crystalline cellulose h was used instead of crystalline cellulose A of the present invention. Results of evaluation of the obtained tablet are shown in Table 4.

Comparative Examples 5 to 8 are results for using a mixture of the publicly known crystalline cellulose. Either of the tensile displacement at break and the relative fluidity index of the crystalline cellulose was out of the range as defined by the present invention. Therefore, the content uniformity was poor since an evaluation value, which was an index of uniformity in content of medicine (spherical granules), exceeded "10" at all times while tableting was performed.

Comparative Example 9

A granule-containing tablet was obtained in the same manner as described in Example 6 except that, as crystalline cellulose, crystalline cellulose f was used instead of crystalline cellulose A. Results of evaluation of the obtained tablet are shown in Table 4.

Comparative Example 10

A granule-containing tablet was obtained in the same manner as described in Example 6 except that, as crystalline cellulose, crystalline cellulose i was used instead of crystalline cellulose A. Results of evaluation of the obtained tablet are shown in Table 4.

Comparative Example 11

A granule-containing tablet was obtained in the same manner as described in Example 6 except that, as crystalline cellulose, commercially available crystalline cellulose (a product of FMC Corporation, Avicel PH-200 (trade name)) (crystalline cellulose j) was used instead of crystalline cellulose A. Results of evaluation of the obtained tablet are shown in Table 4. Also, physical properties of crystalline cellulose j are shown in Table 2.

Comparative Example 12

A granule-containing tablet was obtained in the same manner as described in Example 6 except that, as crystalline cellulose, commercially available crystalline cellulose (a product of Asahi Kasei Chemicals Corporation, Ceolus PH-301 (trade name)) (crystalline cellulose k) was used instead of crystalline cellulose A. Results of evaluation of the obtained tablet are shown in Table 4. Also, physical properties of crystalline cellulose k are shown in Table 2.

Comparative Example 13

A granule-containing tablet was obtained in the same manner as described in Example 6 except that, as crystalline cellulose, commercially available crystalline cellulose (a product of Mingtai Chemical Co., Ltd., COMPRECEL 102QD (trade name)) (crystalline cellulose 1) was used instead of crystalline cellulose A. Results of evaluation of the obtained tablet are shown in Table 4. Also, physical properties of crystalline cellulose 1 are shown in Table 2.

Comparative Example 14

A granule-containing tablet was obtained in the same manner as described in Example 6 except that, as crystalline cellulose, commercially available crystalline cellulose (a product of JRS Pharma, VIVAPUR 101P (trade name)) (crystalline cellulose m) was used instead of crystalline cellulose A. Results of evaluation of the obtained tablet are shown in Table 4. Also, physical properties of crystalline cellulose m are shown in Table 2.

Comparative Examples 9 to 14 are results obtained from an attempt to prepare a granule-containing tablet using the publicly known crystalline cellulose. Either or both of the tensile displacement at break and the relative fluidity index was/were out of the range as defined by the present invention in any of Comparative Examples 9 to 14. Therefore, the content uniformity was poor since an evaluation value, which was an index of uniformity in content of medicine (spherical granules), exceeded "10" at all times while tableting was performed.

Example 13

Preparation of Spherical Granules

Spherical granules containing sodium salicylate were obtained in the same manner as described in Example 6 except that 1.5 kg of spherical core particles made of crystalline cellulose (an average particle diameter of 153 μm and an average ratio of minor axis to major axis of 0.873) were used. The average particle diameter and the average ratio of minor axis to major axis of the obtained granules were 155 μm and 0.880, respectively.

<Preparation and Evaluation of Granule-Containing Tablet>

Then, a granule-containing tablet was obtained in the same manner as described in Example 6 except that the spherical granules containing sodium salicylate thus obtained were used. Results of evaluation are shown in Table 4.

Example 14

Preparation of Spherical Granules

Spherical granules containing sodium salicylate were obtained in the same manner as described in Example 6 except that 1.5 kg of spherical core particles made of crystalline cellulose (an average particle diameter of 394 μm and an average ratio of minor axis to major axis of 0.909) were used. The average particle diameter and the average ratio of minor axis to major axis of the obtained granules were 395 μm and 0.909, respectively.

<Preparation and Evaluation of Granule-Containing Tablet>

Then, a granule-containing tablet was obtained in the same manner as described in Example 6 except that the spherical granules containing sodium salicylate thus obtained were used. Results of evaluation are shown in Table 4.

Example 15

Preparation of Spherical Granules

Spherical granules containing sodium salicylate were obtained in the same manner as described in Example 6 except that 1.5 kg of spherical core particles made of crystalline cellulose (an average particle diameter of 586 μm and an average ratio of minor axis to major axis of 0.901) were used. The average particle diameter and the average ratio of minor axis to major axis of the obtained granules were 587 μm and 0.902, respectively.

<Preparation and Evaluation of Granule-Containing Tablet>

Then, a granule-containing tablet was obtained in the same manner as described in Example 6 except that the spherical granules containing sodium salicylate thus obtained were used. Results of evaluation are shown in Table 4.

Example 16

Preparation of Spherical Granules

Spherical granules containing sodium salicylate were obtained in the same manner as described in Example 6 except that 1.5 kg of spherical core particles made of crystalline cellulose (an average particle diameter of 763 μm and an average ratio of minor axis to major axis of 0.897) were used. The average particle diameter and the average ratio of minor axis to major axis of the obtained granules were 763 μm and 0.900, respectively.

<Preparation and Evaluation of Granule-Containing Tablet>

Then, a granule-containing tablet was obtained in the same manner as described in Example 6 except that the spherical granules containing sodium salicylate thus obtained were used. Results of evaluation are shown in Table 4.

Examples 13 to 16 are results obtained from an attempt to prepare granule-containing tablets with varied granule sizes. Content uniformity was favorable in any of the granule-containing tablets of Examples 13 to 16. However, a tendency was observed based on the obtained results that the uniformity in content was higher when the size of the spherical granules was smaller.

TABLE 1

|  | Crystalline cellulose | Tensile displacement at break (μm) | Relative fluidity index (—) | Remarks |
|---|---|---|---|---|
| Example 1 | A | 58.9 | 2.68 | A mixture of crystalline celluloses a and b at a:b = 3:7 |
| Example 2 | B | 51.0 | 2.49 | A mixture of crystalline celluloses a and b at a:b = 2:8 |
| Example 3 | C | 59.8 | 2.19 | A mixture of crystalline celluloses a and c at a:c = 6:4 |
| Example 11 | D | 65.5 | 2.34 | A mixture of crystalline celluloses b and f at b:f = 4:6 |
| Example 12 | E | 29.1 | 2.62 | A mixture of crystalline celluloses b and i at b:i = 4:6 |
| Comparative Example 5 | d | 62.4 | 3.02 | A mixture of crystalline celluloses a and b at a:b = 4:6 |
| Comparative Example 6 | e | 31.3 | 3.41 | A mixture of crystalline celluloses a and b at a:b = 1:9 |
| Comparative Example 7 | g | 93.3 | 2.22 | A mixture of crystalline celluloses b and f at b:f = 3:7 |
| Comparative Example 8 | h | 58.0 | 1.93 | A mixture of crystalline celluloses b and f at b:f = 5:5 |

TABLE 2

|  | Crystalline cellulose | Average particle diameter (μm) | Average ratio of minor axis to major axis (—) | Tensile displacement at break (μm) | Relative fluidity index (no unit) | Remarks |
|---|---|---|---|---|---|---|
| Comparative Example 1 | a | 49 | 0.357 | 83.5 | 1.83 | A raw material for crystalline celluloses A, B, C, d and e |
| Comparative Example 2 | b | 172 | 0.726 | 41.0 | 3.29 | A raw material for crystalline celluloses A, B, D, E, d, e, g and h |
| Comparative Example 3 | c | 98 | 0.647 | 44.4 | 3.12 | A raw material for crystalline cellulose C |
| Comparative Example 9 | f | 51 | 0.290 | 110.0 | 1.81 | A raw material for crystalline celluloses D, h and g |
| Comparative Example 10 | i | 50 | 0.556 | 60.5 | 1.99 | A raw material for crystalline cellulose E |
| Comparative Example 11 | j | 181 | 0.644 | 66.3 | 2.95 | A commercial product |
| Comparative Example 12 | k | 46 | 0.628 | 98.3 | 2.29 | A commercial product |
| Comparative Example 13 | l | 65 | 0.447 | 40.7 | 2.12 | A commercial product |
| Comparative Example 14 | m | 51 | 0.502 | 87.0 | 2.00 | A commercial product |

TABLE 3

|  | Sampling | Hardness (N) | Degree of abrasion (%) | Disintegration time (s) | Weight variability (%) | Content of medicine (%) | Variability in content of medicine (%) | Evaluation value (no unit) |
|---|---|---|---|---|---|---|---|---|
| Example 1 | Initial period | 69.8 | 0.03 | 93 | 0.66 | 101.1 | 0.90 | 2.1 |
|  | Intermediate period | 72.9 | 0.04 | 104 | 0.78 | 101.1 | 1.39 | 3.4 |
|  | Late period | 75.9 | 0.00 | 108 | 0.86 | 99.7 | 1.15 | 2.7 |
| Example 2 | Initial period | 69.5 | 0.05 | 99 | 0.54 | 101.4 | 1.20 | 9.6 |
|  | Intermediate period | 71.6 | 0.02 | 86 | 0.68 | 100.2 | 1.10 | 9.9 |
|  | Late period | 71.0 | 0.03 | 95 | 0.67 | 98.8 | 1.00 | 8.9 |
| Example 3 | Initial period | 81.4 | 0.01 | 110 | 0.85 | 102.3 | 1.80 | 5.3 |
|  | Intermediate period | 80.7 | 0.02 | 106 | 0.79 | 97.2 | 1.07 | 4.6 |
|  | Late period | 84.2 | 0.01 | 123 | 0.99 | 99.1 | 1.74 | 6.5 |

TABLE 3-continued

|  | Sampling | Hardness (N) | Degree of abrasion (%) | Disintegration time (s) | Weight variability (%) | Content of medicine (%) | Variability in content of medicine (%) | Evaluation value (no unit) |
|---|---|---|---|---|---|---|---|---|
| Example 4 | Initial period | 73.9 | 0.01 | 155 | 0.68 | 102.1 | 1.49 | 3.6 |
|  | Intermediate period | 74.3 | 0.03 | 134 | 0.87 | 98.3 | 1.35 | 4.7 |
|  | Late period | 71.2 | 0.00 | 141 | 0.71 | 99.6 | 1.24 | 3.1 |
| Example 5 | Initial period | 61.3 | 0.04 | 88 | 0.75 | 101.9 | 1.45 | 3.9 |
|  | Intermediate period | 59.8 | 0.06 | 82 | 0.81 | 98.6 | 1.79 | 4.3 |
|  | Late period | 62.1 | 0.03 | 84 | 0.87 | 100.8 | 1.64 | 3.9 |
| Comparative Example 1 | Initial period | 61.1 | 0.07 | 90 | 1.01 | 108.1 | 2.15 | 11.9 |
|  | Intermediate period | 56.3 | 0.11 | 85 | 0.88 | 108.6 | 1.89 | 11.8 |
|  | Late period | 57.4 | 0.09 | 85 | 121 | 109.6 | 2.02 | 15.3 |
| Comparative Example 2 | Initial period | 87.1 | 0.01 | 95 | 0.40 | 113.1 | 2.17 | 16.9 |
|  | Intermediate period | 88.3 | 0.00 | 91 | 0.44 | 111.2 | 1.75 | 15.1 |
|  | Late period | 83.7 | 0.02 | 83 | 0.67 | 107.5 | 2.24 | 11.3 |
| Comparative Example 3 | Initial period | 57.5 | 0.96 | 83 | 0.85 | 105.5 | 1.60 | 10.2 |
|  | Intermediate period | 51.3 | 1.01 | 79 | 0.56 | 104.2 | 2.30 | 9.7 |
|  | Late period | 52.4 | 0.98 | 79 | 1.05 | 106.1 | 1.59 | 11.6 |
| Comparative Example 4 | Initial period | 49.8 | 1.21 | 158 | 1.05 | 110.8 | 2.18 | 15.1 |
|  | Intermediate period | 51.8 | 1.08 | 167 | 0.82 | 108.7 | 1.77 | 17.8 |
|  | Late period | 48.7 | 1.33 | 155 | 0.71 | 105.8 | 2.08 | 9.6 |

TABLE 4

|  | Crystalline cellulose | Evaluation value (no unit) | | |
|---|---|---|---|---|
|  |  | Initial period | Intermediate period | Late period |
| Example 6 | A | 2.5 | 2.3 | 2.6 |
| Example 7 | A | 6.3 | 6.3 | 9.1 |
| Example 8 | A | 4.8 | 5.2 | 5.7 |
| Example 9 | B | 8.5 | 8.8 | 7.9 |
| Example 10 | C | 4.9 | 2.1 | 6.3 |
| Example 11 | D | 9.8 | 9.2 | 9.4 |
| Example 12 | E | 7.7 | 8.2 | 7.6 |
| Example 13 | A | 3.4 | 2.4 | 3.9 |
| Example 14 | A | 7.9 | 9.4 | 8.9 |
| Example 15 | A | 9.8 | 8.7 | 9.6 |
| Example 16 | A | 13.5 | 9.2 | 11.5 |
| Comparative Example 5 | d | 11.6 | 10.9 | 11.0 |
| Comparative Example 6 | e | 25.0 | 22.4 | 25.0 |
| Comparative Example 7 | g | 11.9 | 11.8 | 13.1 |
| Comparative Example 8 | h | 12.6 | 13.1 | 11.7 |
| Comparative Example 9 | f | 15.2 | 16.4 | 15.8 |
| Comparative Example 10 | i | 12.3 | 14.1 | 13.9 |
| Comparative Example 11 | j | 13.3 | 15.0 | 16.1 |
| Comparative Example 12 | k | 16.9 | 18.1 | 20.3 |
| Comparative Example 13 | l | 12.2 | 12.1 | 14.2 |
| Comparative Example 14 | m | 13.8 | 12.1 | 14.6 |

INDUSTRIAL APPLICABILITY

The present invention can be preferably used in a field of production of a sustained-release preparation containing a pharmaceutical medicine.

The present invention can be preferably used in a field related to production of a tablet containing a granular agent for a pharmaceutical preparation, particularly film-coated granules.

The invention claimed is:
1. A process for producing a granule-containing tablet comprising
mixing
more than 25 mass % to 89 mass % of a first crystalline cellulose consisting of
a) relatively spherical cellulose with an average ratio of minor axis to major axis of approximately 0.6 or more and
b) relatively rod-shaped crystalline cellulose with an average ratio of minor axis to major axis of less than 0.6, and exhibiting a tensile displacement at break of 25 to 80 μm and a relative fluidity index of 2.15 to 2.80 at a maximum compaction stress of 15 kPa,
10 to 70 mass % of spherical granules, and
20 mass % or less of a disintegrant, and then
compressing the obtained mixture.
2. The method for producing the granule-containing tablet according to claim 1, wherein the tensile displacement at break is 30 to 65 μm.
3. The method for producing the granule-containing tablet according to claim 1, wherein the relative fluidity index is 2.55 to 2.75.
4. The method for producing the granule-containing tablet according to claim 1, wherein the disintegrant is partially-pregelatinized starch.
5. The method for producing the granule-containing tablet according to claim 1, wherein the spherical granules are film-coated granules.
6. The method for producing the granule-containing tablet according to claim 5, wherein the film-coated granules comprise spherical core particles containing 70 mass % or more of a second crystalline cellulose component, a medicine layer coating the periphery of the spherical core particles, and a film coating the periphery of the medicine layer.

7. The method for producing the granule-containing tablet according to claim 5, wherein the average particle diameter of the film-coated granules is 300 μm or less.

8. A granule-containing tablet obtained by the method according to claim 1.

9. A granule-containing tablet comprising
more than 25 mass % to 89 mass % of crystalline cellulose consisting of
   a) relatively spherical cellulose with an average ratio of minor axis to major axis of approximately 0.6 or more and
   b) relatively rod-shaped crystalline cellulose with an average ratio of minor axis to major axis of less than 0.6, and exhibiting a tensile displacement at break of 25 to 80 μm and a relative fluidity index of 2.15 to 2.80 at a maximum compaction stress of 15 kPa,
10 to 70 mass % of spherical granules, and
20 mass % or less of a disintegrant.

10. A crystalline cellulose excipient for a granule-containing tablet, wherein the crystalline cellulose excipient comprises
more than 25 mass % to 89 mass % of crystalline cellulose consisting of
   a) relatively spherical cellulose with an average ratio of minor axis to major axis of approximately 0.6 or more and
   b) relatively rod-shaped crystalline cellulose with an average ratio of minor axis to major axis of less than 0.6, and exhibiting a tensile displacement at break of 25 to 80 μm and a relative fluidity index of 2.15 to 2.80 at a maximum compaction stress of 15 kPa, and
20 mass % or less of a disintegrant.

11. A method for producing an excipient for a granule-containing tablet, which comprises
mixing
   40-80 mass % of relatively spherical crystalline cellulose with an average ratio of minor axis to major axis of approximately 0.6 or more, and
   20-60 mass % of relatively rod-shaped crystalline cellulose with an average ratio of minor axis to major axis of less than 0.6, and
preparing a crystalline cellulose composition comprising
   more than 25 mass % to 89 mass % of the obtained crystalline cellulose exhibiting a tensile displacement at break of 25 to 80 μm and a relative fluidity index of 2.15 to 2.80 at a maximum compaction stress of 15 kPa, and
   20 mass % or less of a disintegrant,
as an excipient for a granule-containing tablet.

* * * * *